United States Patent [19]

Mehta

[11] 4,417,064
[45] Nov. 22, 1983

[54] BIPHENYL COMPOUNDS AND METHOD OF PREPARING SAME

[75] Inventor: Avinash C. Mehta, Belmont, Mass.
[73] Assignee: Polaroid Corporation, Cambridge, Mass.
[21] Appl. No.: 313,944
[22] Filed: Oct. 22, 1981

Related U.S. Application Data

[63] Continuation-in-part of Ser. No. 222,682, Jan. 5, 1981, abandoned.
[51] Int. Cl.³ .................. C07D 309/12; C07C 69/017; C07C 43/205
[52] U.S. Cl. .................................... 549/415; 568/746; 568/643; 568/592; 568/331; 568/49; 568/47; 560/255; 560/108; 549/472; 260/463
[58] Field of Search ............... 568/746, 643, 592, 331, 568/49, 47; 260/463; 560/108, 255; 549/415, 472

[56] References Cited

U.S. PATENT DOCUMENTS

| | | | |
|---|---|---|---|
| 3,406,064 | 10/1968 | Land | 96/29 |
| 3,600,177 | 8/1971 | Abbott et al. | 96/76 |
| 3,617,272 | 11/1971 | Stewart | 96/3 |
| 3,617,277 | 11/1971 | Stewart | 96/29 D |
| 4,279,987 | 7/1981 | Ogi et al. | 430/409 |

OTHER PUBLICATIONS

Misiorny et al., Acta Pharm. Suecia, 14, 105, (1977).
Morrison and Boyd, "Organic Chemistry", 3rd Ed., Allyn and Bacon Inc., Boston, 1973, pp. 386–389.
Offermann et al., Synthesis, Apr. 1977, pp. 272–273.
Friedrich et al., J. Org. Chem. 34, 900, (1969).

*Primary Examiner*—Nicky Chan
*Attorney, Agent, or Firm*—Louis G. Xiarhos

[57] ABSTRACT

The present invention relates to novel biphenyl compounds of the formula

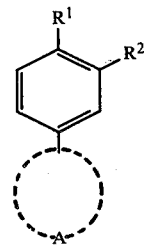

wherein one of $R^1$ and $R^2$ is hydrogen and the other is —$CH_{3-m}X_m$ wherein X is chloro or bromo and m is an integer one or two, and the cyclic moiety A is a -2,5-; -2,3-; or -3,4-di-OR-1-phenyl moiety wherein R is a hydroxy-protecting group and to a method of preparing same. The biphenyl compounds are useful as intermediates in preparing redox compounds containing a phenylhydroquinone or phenylcatechol moiety.

16 Claims, No Drawings

BIPHENYL COMPOUNDS AND METHOD OF PREPARING SAME

CROSS-REFERENCE TO RELATED PATENT APPLICATION

This application is a continuation-in-part of application Ser. No. 222,682, filed Jan. 5, 1981, and now abandoned.

BACKGROUND OF THE INVENTION

The present invention relates to novel compounds and to a method for preparing same. More particularly, it relates to intermediate compounds useful in preparing redox reagents comprising a phenylhydroquinone or phenylcatechol moiety.

Compounds having phenylhydroquinone or phenylcatechol moieties are of interest for employment as redox reagents, i.e., as reducing or electron-transfer agents in redox reactions. For example, such compounds are of interest in the photographic art for employment as redox reagents in photographic products and processes, e.g., as silver halide developing agents or auxiliary developing agents. The compound 4-phenylcatechol, for example, is disclosed in U.S. Pat. Nos. 3,617,272 and 3,617,277 to be useful as an auxiliary developing agent and as a chelating agent in certain diffusion transfer photographic elements. 4'-Methylphenylhydroquinone is a particularly useful compound which has been employed in various applications in diffusion transfer photographic processes. U.S. Pat. No. 3,406,064 discloses the use of 4'-methylphenylhydroquinone as a silver halide developing agent in diffusion transfer processes for forming silver images. The employment of 4'-methylphenylhydroquinone as an auxiliary developing agent in color diffusion transfer processes is well known and is described by E. H. Land in Photographic Journal, 114, 338 (1974).

With regard to the photographic utility of compounds containing phenylhydroquinone or phenylcatechol moieties, it is believed that the biphenyl ring structure of these moieties contributes redox properties to the compounds rendering them particularly suitable for employment in various photographic applications. Accordingly, there has been a desire in the photographic art to provide compounds containing a phenylhydroquinone or phenylcatechol moiety such that the redox characteristics normally exhibited by these moieties may be used to advantage.

SUMMARY OF THE INVENTION

The present invention relates to novel intermediate compounds that can be reacted to prepare a wide variety of product compounds containing a phenylhydroquinone or phenylcatechol moiety. In particular, the present invention relates to biphenyl compounds of the formula

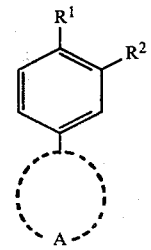

wherein one of $R^1$ and $R^2$ is hydrogen and the other is $-CH_{3-m}X_m$ wherein X is chloro or bromo and m is an integer one or two, and the cyclic moiety A is a -2,5-; -2,3-; or -3,4-di-OR-1-phenyl moiety wherein R is a hydroxy-protecting group. The biphenyl compounds of this invention are useful intermediates in that they can be reacted through the group $-CH_{3-m}X_m$, either in a single reaction step or a series of reaction steps, to prepare materials which can be deblocked to remove the R groups, thereby providing redox compounds containing a phenylhydroquinone or phenylcatechol moiety. Compounds containing such moieties can be employed as redox reagents, e.g., as antioxidants or as developing agents in photographic processes.

In a preferred embodiment, the compounds of this invention are of the formula

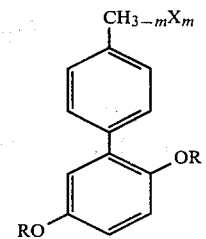

wherein X, R and m are as previously defined.

In its method aspect, the present invention provides a process for preparing the compounds of this invention which comprises (a) blocking the hydroxy groups of a 3'- or 4'-methyl-x,y-dihydroxy-1,1'-biphenyl, wherein -x,y- is -2,5-; -2,3-; or -3,4-, with a hydroxy-protecting group to form the corresponding 3'- or 4'-methyl -x,y-di-OR-1,1'-biphenyl, wherein R is the hydroxy-protecting group; and (b) reacting the 3'- or 4'-methyl -x,y-di-OR-1,1'-biphenyl with a benzylic halogenating agent to form the corresponding 3'- or 4'-halomethyl or dihalomethyl-x,y-di-OR-1,1'-biphenyl.

For a fuller understanding of the present invention, reference should be had to the following detailed description.

DETAILED DESCRIPTION OF THE INVENTION

As indicated previously, the present invention relates to compounds which can be employed as intermediates in the preparation of compounds containing a phenylhydroquinone moiety, and specifically a moiety of the formula

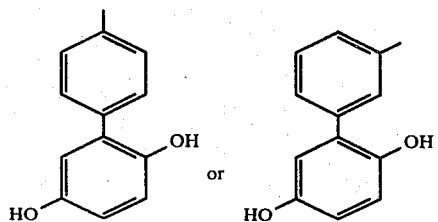

or a phenylcatechol moiety, specifically a moiety of the formula

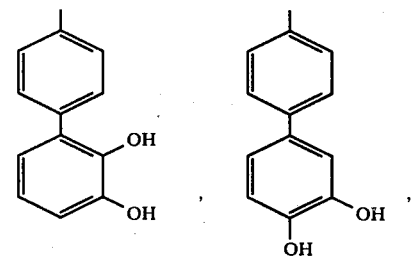

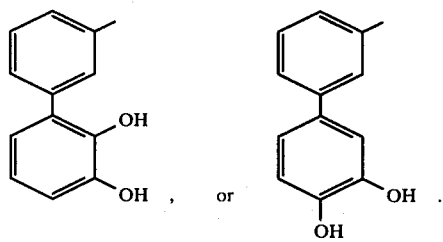

In the above formulas, the unattached valence bond shows the point of attachment of the moiety to the remainder of the redox compound.

The compounds of this invention are of the formula

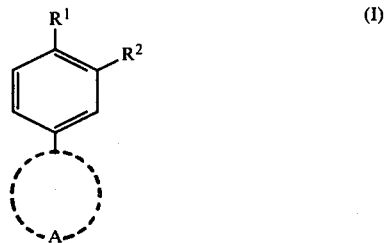

wherein one of $R^1$ and $R^2$ is hydrogen and the other is —$CH_{3-m}X_m$ wherein X is chloro or bromo and m is an integer one or two, and the cyclic moiety A is a -2,5-; -2,3-; or -3,4-di-OR-1-phenyl moiety, i.e., a moiety of the formula

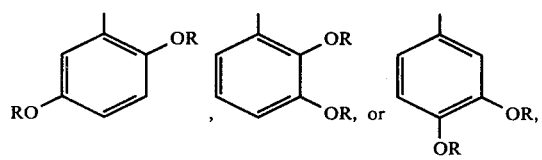

wherein R is a hydroxy-protecting group. In accordance with formula (I), the compounds of this invention can be referred to as 3'- or 4'-halomethyl or dihalometh-yl-x,y-di-OR-1,1'-biphenyls wherein -x,y is -2,5-; -2,3-; or 3,4-.

The cyclic moiety A of the compounds of this invention may be substituted with substituents in addition to the —OR groups. Such substituents should be stable to and compatible with the reagents and reaction conditions employed in subsequent reactions of the instant compounds. Such substituents and the substitution pattern thereof on a compound of this invention will generally affect the oxidation-reduction potential of a redox material ultimately prepared from the compound. Generally, electron-attracting substituents will increase the redox potential of the material and electron-donating groups will lower it. Substituents in addition to —OR which may be present in the cyclic moiety A include low alkoxy, nitro, cyano, carboxy, sulfo, formyl, chloro, bromo, and iodo, as well as carboxamido groups, e.g.,

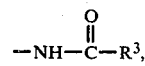

and acyl groups, e.g.,

wherein $R^3$ and $R^4$ are alkyl.

The hydroxy-protecting groups selected for use in the present invention should be capable of protecting the hydroxy groups either during preparation or reaction of the instant compounds such that the —OR groups are preserved intact until it is desired to remove the protecting groups to regenerate the hydroxy moieties. Suitable protecting groups are those capable of providing such protection and also capable of undergoing desired removal under either acidic, neutral, or basic conditions so as to regenerate the hydroxy groups. Inasmuch as the intermediates of this invention are intended to be reacted to prepare materials from which the hydroxy-protecting groups are to be removed, the hydroxy-protecting groups should be capable of removal under conditions appropriate for such a material, e.g., the material may be insoluble or unstable in the presence of acid such that employment of protecting groups capable of removal under neutral or basic conditions will generally be preferred. In addition to considerations regarding the above-described protection of the hydroxy groups during preparation and reaction of the instant compounds and the conditions under which a protecting group can be removed, the choice of a particular protecting group can depend on factors such as the ease with which a compound of this invention may be prepared to comprise a given protecting group, the degree of difficulty of removal of the protecting group to regenerate the hydroxy groups, and the effect of the protecting group on the reactivity of the cyclic moiety A, either during the preparation of the instant compounds or during subsequent reactions thereof. Among the various groups which may be employed herein as hydroxy-protecting groups, specific mention may be made of lower alkyl having 1 to 6 carbon atoms such a methyl, ethyl, isopropyl, and tert-butyl; methoxymethyl; methylthiomethyl; phenacyl; p-bromophenacyl; 2-tetrahydrofuranyl; 2-tetrahydropyranyl; ethoxycarbonyl; 2,2,2-trichloroethoxycarbonyl; and acyl, e.g., acetyl and benzoyl.

With regard to the substituent —CH$_{3-m}$X$_m$, if m is one the substituent is referred to as a monohalomethyl substituent and if m is 2 the substituent is referred to as a dihalomethyl substituent. As used herein, the term monohalomethyl refers to chloromethyl and bromomethyl and the term dihalomethyl refers to dichloromethyl and dibromomethyl. Those compounds of this invention wherein m is one are referred to herein as either monohalomethyl or benzyl derivatives, the 3' or 4'-monohalomethylphenyl ring being essentially a benzyl halide moiety, whereas those compounds wherein m is two are referred to as either dihalomethyl or benzal derivatives, the 3' or 4'-dihalomethylphenyl ring being essentially a benzal halide moiety. As shown in formula (I), the monohalomethyl or dihalomethyl substituent may be positioned at either the 3'- or 4'-position of the biphenyl ring structure.

Specific examples of the compounds of this invention include:

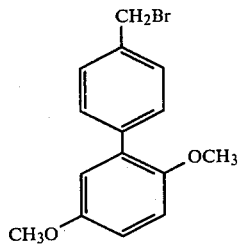
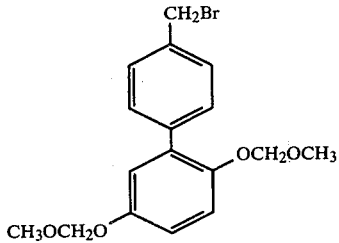
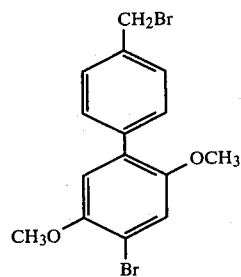
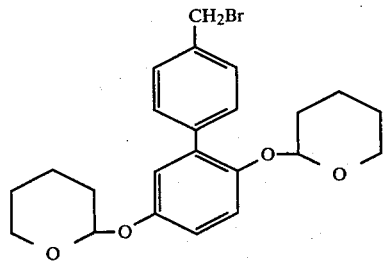
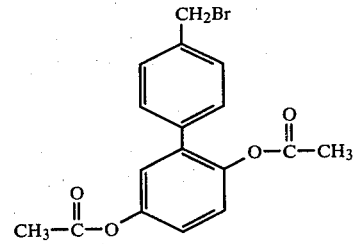
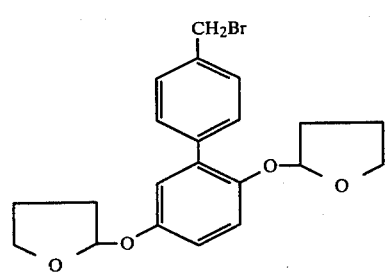
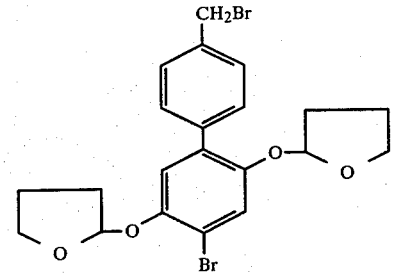
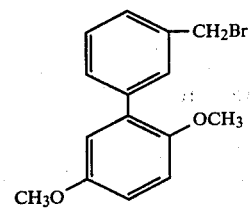
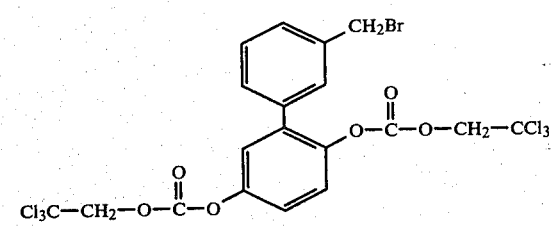
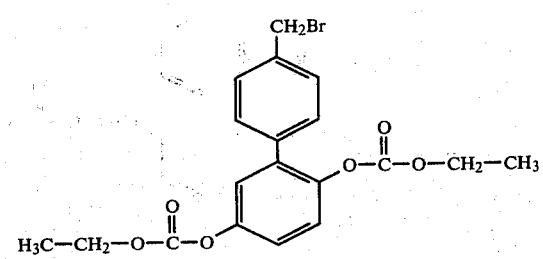

-continued
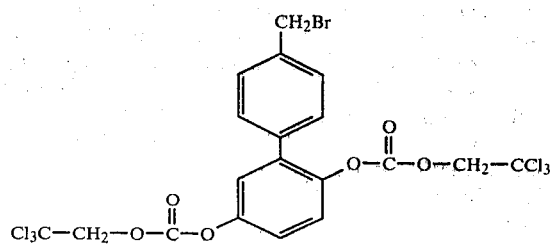
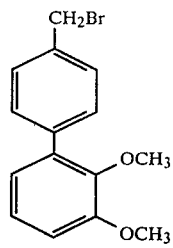
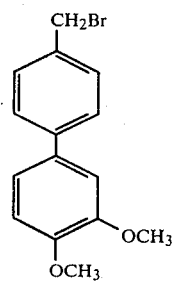
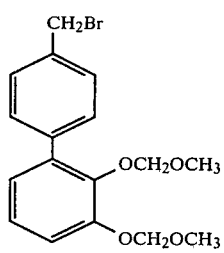
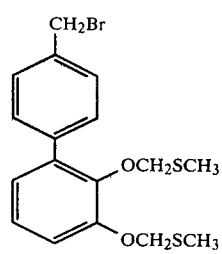
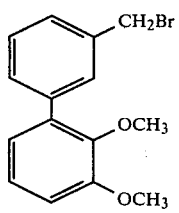
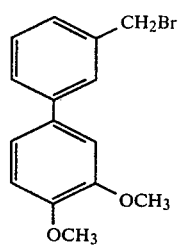
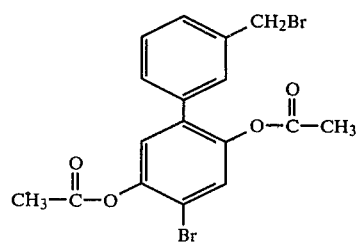
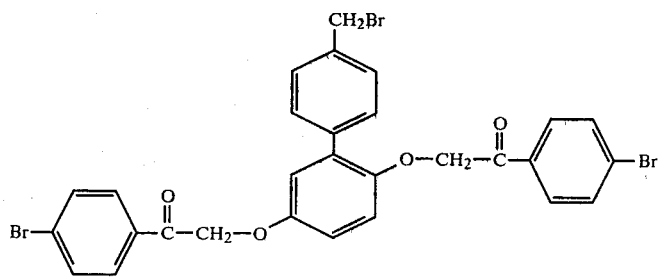

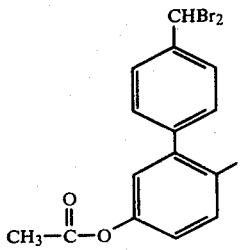
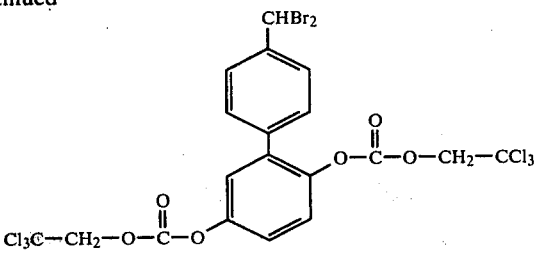
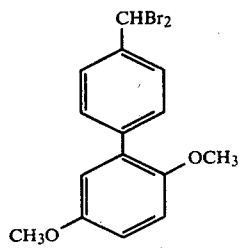
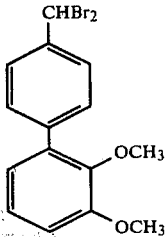
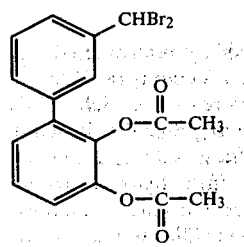
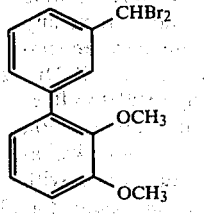

Preferred compounds of this invention are those of the formula

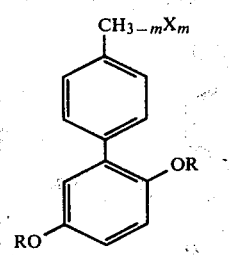

wherein X, R, and m are as previously defined. These preferred compounds provide the capability of preparing compounds comprising a 4'-methylene-2,5-dihydroxy-1,1'-biphenyl moiety, i.e., a 4'-methylenephenylhydroquinone moiety, and thus allow provision of materials comprising a redox moiety analogous to 4'-methylphenylhydroquinone. As previously indicated, 4'-methylphenylhydroquinone has proven to be a particularly useful redox reagent in diffusion transfer photographic processes.

The compounds of this invention can be prepared by blocking the hydroxy groups of a 3'- or 4'-methyl-x,y-dihydroxy-1,1'-biphenyl with a hydroxy-protecting group to form the corresponding 3'- or 4'-methyl-x,y-di-OR-1,1'-biphenyl wherein x, y is -2,5-; -2,3-; or -3,4- and R is a hydroxy-protecting group, and reacting the 3'- or 4'-methyl-x,y-di-OR-1,1'-biphenyl with a benzylic chlorinating or brominating agent to prepare the corresponding 3'- or 4'-halomethyl or dihalomethyl-x,y-di-OR-1,1'-biphenyl. In general, the halomethyl or benzyl compounds can be satisfactorily prepared by reacting the 3'-or 4'-methyl-x,y-di-OR-1,1'-biphenyl and benzylic chlorinating or brominating agent in a molar ratio of about 1:1, whereas the dihalomethyl or benzal compounds can be satisfactorily prepared by reacting the aforesaid materials in a molar ratio of about 1:2 respectively. This method of preparation is illustrated below employing, as specific reagents, 4'-methyl-2-5-dihydroxy-1,1'biphenyl as the starting material, acetic anhydride and sulfuric acid as the reagents used to effect blocking of the hydroxy groups, and N-bromosuccinimide (NBS) as a benzylic brominating agent:

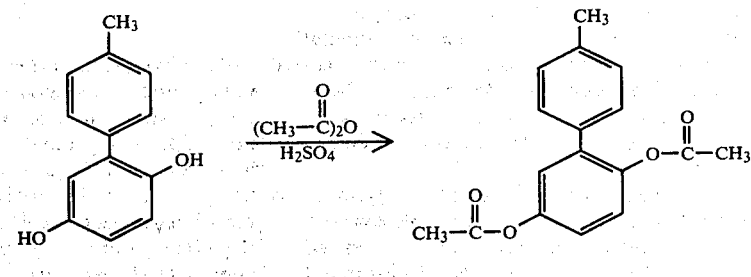

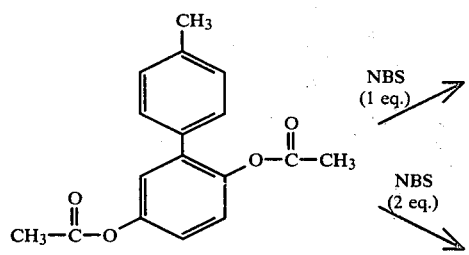 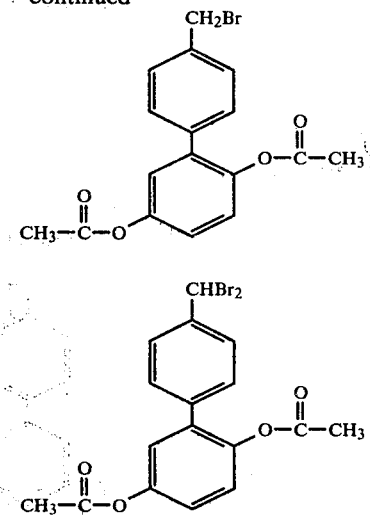

Methods of blocking hydroxy groups with removable protecting groups are well known in the art and any suitable method of accomplishing same may be employed to produce the 3'- or 4'-methyl-x,y-di-OR-1,1'-biphenyls. Methods which may be employed to effect blocking of the hydroxy groups include methylation with dimethylsulfate in the presence of aqueous alkali as described in Example 1 hereinafter; acylation with acetic anhydride in the presence of an acid catalyst as illustrated above and as and as described in Example 2 hereinafter; methoxy methylation as described, for example, by Kaoru Fuji et al., Synthesis, 4, pp. 276–277 (1975); tetrahydrofuranylation as described, for example, by C. G. Kruse et al., Tetrahedron Lett., 20, p. 1725 (1976); tetrahydropyranylation as described, for example, by W. F. Parham et al., J. Am. Chem. Soc., 70, pp. 4187–4189 (1948); and trichloroethoxycarbonylation as described, for example, by Just et al., Synthesis, p. 457, (1976).

The chlorination or bromination of the 3'- or 4'-methyl-x,y-di-OR-1,1'-biphenyl is effected by reaction of this material with a benzylic chlorinating or brominating agent, i.e., an agent capable of effecting chlorination or bromination of the substituent methyl group to produce the $CH_{3-m}X_m$ substituent. Such agents are hereinafter referred to collectively as benzylic halogenating agents and the chlorination or bromination reaction as a benzylic halogenation reaction. Although the agents and reaction are referred to as "benzylic", it will be understood that production of a benzal compound as well as a benzyl compound can be effected thereby. Any halogenating agent capable of effecting the desired chlorination or bromination may be used as the benzylic halogenating agent of the present process, provided that it does not degrade the biphenyl compound or effect chlorination or bromination of either of the phenyl rings thereof to an unacceptable extent. Benzylic halogenating agents which may be employed include elemental bromine and chlorine, sulfuryl chloride, N-bromosaccharin, tetramethylammoniumtribromide, N,N-dibromobenzenesulfonamide, bromotrichloromethane, and carbon tetrabromide. A preferred benzylic halogenating agent is N-bromosuccinimide.

It will be understood that blocking the hydroxy groups prior to conducting the benzylic halogenation reaction greatly facilitates provision of the desired product. Benzylic halogenation of a methyl substituent in an aromatic compound containing unprotected phenolic hydroxy groups generally is accompanied by undesired side reactions which decrease the yield of the desired product and complicate or prevent its isolation in a substantially pure state. These side reactions are largely avoided by the blocking of the hydroxy groups.

In the conduct of the halogenation reaction, nuclear or ring halogenation may occur in addition to, or in lieu of, benzylic halogenation, thus producing a mixture of halogenated products. For example, monobromination of 4'-methyl-2,5-dimethoxy-1,1'-biphenyl can produce a mixture comprising the following three products:

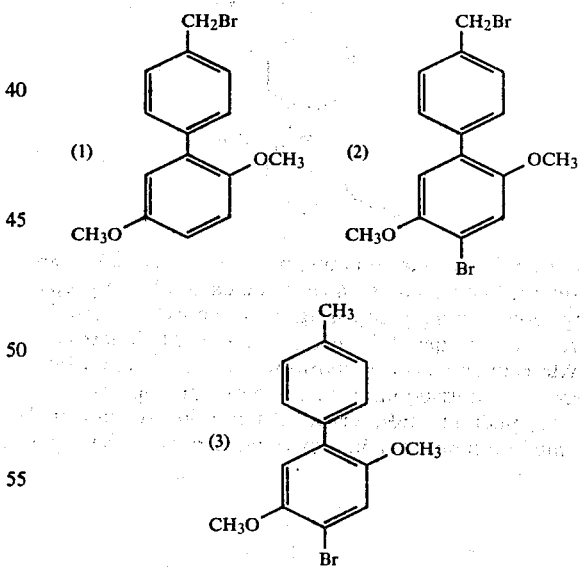

Ring halogenation may be desirable in terms of providing certain halogen substituted end products, i.e., halogen substituted redox materials obtained by reaction of the compounds of this invention. In general, however, it will be desired to minimize ring halogenation so as to obtain a maximum yield of a benzylic halogenation product free of aromatic halogen substituents. Ring halogenation may be minimized by methods well known in the art, e.g., use of reactants and reaction conditions which promote the formation of bromine or chlorine radicals and, thus, promote benzylic halogenation. Accordingly, the benzylic halogenation reaction is preferably conducted in an anhydrous organic solvent containing a free radical initiator, such as dibenzoyl peroxide or axobisisobutyronitrile, such conditions tending to promote formation of chlorine and bromine radicals.

Ring halogenation may also be minimized by employment of hydroxy-protecting groups which tend to deactivate the cyclic moiety A toward halogenation. In particular, protecting groups which withdraw electrons from the resonance system of the 1-phenyl ring will generally deactivate the moiety A such that ring halogenation thereof is minimized or essentially non-occurring. The desired 3'- or 4'-halomethyl or dihalomethyl-x,y-di-OR-1,1'-biphenyl may thus be prepared in high yield and essentially free of ring-halogenated contaminants. Accordingly, from the standpoint of minimization of ring halogenation in the preparation of the compounds hereof, the employment of electron-withdrawing hydroxy-protective groups constitutes a preferred practice of this invention. Electron-withdrawing protective groups which may be employed herein include the previously mentioned acyl, ethoxycarbonyl, and 2,2,2-trichloroethoxycarbonyl groups.

Should ring halogenation occur to an unacceptable extent, ring halogenated products may be removed or segregated by any suitable technique commonly employed in the chemical art to effect purification, e.g., recrystallization or chromotographic techniques. The ring halogenated products may be segregated from the product mix obtained by conduct of the benzylic halogenation reaction. Generally, however, it will prove desirable to react such a product mix in toto to produce a second product mix from which one or more ring-halogenated products may be removed with greater facility. Such a procedure may prove especially beneficial where the reaction of the product mix produces reaction product materials having dissimilar physical properties, such as solubility or diffusibility, which facilitates separation of the product materials. For example, it is disclosed in the copending U.S. Pat. application Ser. No. 222,361 of A. C. Mehta, filed Jan. 5, 1981, that reaction of the above illustrated representative mixture, comprising materials (1), (2), and (3), with a triarylphosphine such as triphenylphosphine converts materials (1) and (2) to phosphonium halide salts which precipitate from an organic solvent system while compound (3), which is not capable of conversion to a phosphonium halide salt, remains solubilized in such a solvent system. It is also disclosed in the cited copending application that the phosphonium halide salts of compounds (1) and (2) may be converted to the corresponding vinyl compounds which may be separated by techniques such as recrystallization or column chromatography.

The halogenation reaction may be conducted in any inert organic solvent known in the art to be useful in the conduct of a benzylic halogenation reaction. In order to minimize ring halogenation, the solvent system should be substantially free of components which promote formation of positive halogen ions, said ions being generally recognized as effecting aromatic ring halogenation. For example, relatively small amounts of water in the organic solvent may substantially increase the formation of positive halogen ions and, thus, the incidence of ring halogenation. Accordingly, consistent with the objective of minimizing ring halogenation, solvents used in the halogenation reaction should be substantially anhydrous. Solvents which may be employed include methyl formate, benzene, and mixtures of methylacetate/dichloromethane. A particularly preferred solvent is carbon tetrachloride.

The amount of benzylic halogenating agent employed in the halogenation reaction will generally vary with the degree of halogenation desired, i.e., as appropriate for production of a desired benzyl or benzal compound. The amount of halogenating agent may also vary with the particular halogenating agent or the particular biphenyl material to be reacted. In general, as noted previously, the benzyl derivatives can be satisfactorily prepared by reacting the 3'- or 4'-methyl-x,y-di-OR-1,1'-biphenyl and benzylic halogenating agent in a molar ratio of about 1:1, whereas the benzal derivatives can be satisfactorily prepared by reacting the aforesaid materials in a molar ratio of about 1:2 respectively.

A mentioned previously, the compounds of this invention can be reacted through the group $CH_{3-m}X_m$, either in a single reaction step or a series of reaction steps, to prepare materials which can be deblocked to remove the hydroxy-protecting groups and provide redox materials containing a phenylhydroquinone or phenylcatechol moiety. The $CH_{3-m}X_m$ group is an especially useful group for such purpose in that it is highly reactive and, in general, is capable of participation in any of a wide variety of known reactions of benzyl or benzal chloride or bromide moieties. Thus, for example, a compound of this invention may be reacted with nucleophilic compounds, such as alcohols and and amines, to prepare desired derivatives. One application of the compounds of this invention is in the production of useful redox polymers. For example, the benzyl compounds of this invention can be reacted with a triarylphosphine to prepare a triarylphosphonium halide salt which can be reacted with formaldehyde in the presence of a strong base to prepare a vinyl biphenyl, i.e., a 3'- or 4'-vinyl-x,y-di-OR-1,1'-biphenyl wherein -x,y- is -2,5-; -2,3-; or -3,4-. The vinyl biphenyl can be polymerized and the resultant "blocked" polymer deblocked to provide the desired redox polymer, i.e., a poly(3'- or 4'-vinyl-x,y-dihydroxy-1,1'-biphenyl). The vinyl biphenyl and the method of preparing same as described hereinabove are disclosed and claimed in the previously cited copending U.S. application Ser. No. 222,361 of A. C. Mehta, filed Jan. 5, 1981. Also disclosed and claimed therein are the aforementioned "blocked" and redox polymers and the method of preparing same from a vinyl biphenyl compound.

U.S. patent application Ser. No. 313,942, now U.S. Pat. No. 4,365,072, of A. C. Mehta, filed of even date, discloses and claims 3'- or 4'-formyl-x,y-di-OR-1,1'-biphenyls and 3'- or 4'-formyl-x,y-dihydroxy-1,1'-biphenyls and methods of preparing same employing either the benzal or benzyl halide compounds of this invention. As disclosed therein and as illustrated by Examples 5 and 6 herein, the benzyl and benzal halide compounds of this invention can be converted to the corresponding formyl compounds utilizing well known reagents and reaction procedures. Hydroxy-protecting groups possessing sufficient lability under the conditions of the reaction may be split off so as to provide a 3'- or 4'-formyl-x,y-dihydroxy-1,1'-biphenyl or the hydroxy-protecting group may be one which is maintained intact during the reaction to provide the corresponding 3'- or 4'-formyl-x,y-di-OR-1,1'-biphenyl. As further disclosed in the cited copending application, the formyl group can, in general, undergo the numerous reactions of aromatic aldehyde functions, such that a wide variety of redox materials containing a phenylhydroquinone or phenylcatechol moiety can be prepared. One such application is the preparation of redox reactive polymeric acetals by reaction of the formyl group of a 3'- or 4'-formyl-x,y-dihydroxy-1,1'-biphenyl with a polymeric alcohol such as polyvinylalcohol.

In general, those procedures commonly used in the art for removal of hydroxy-protecting groups may be employed in deblocking the hydroxy groups in derivatives obtained by reaction of the compounds of this invention. The deblocking may be conducted under either acidic, neutral, or basic conditions, as appropriate for the derivative and as appropriate for a given protecting group. Generally it will be desirable to conduct the deblocking reaction under an inert atmosphere to minimize the possibility of oxidation of the phenylhydroquinone or phenylcatechol moiety. The deblocking may be conducted in conjunction with reaction of the benzyl or benzal halide moiety, depending on the nature of the protective group and on the reaction conditions employed. Deblocking at this juncture in a synthetic sequence can be tolerated, provided that the regeneration of the hydroxy groups is consonant with the intended reaction of the benzyl or benzal halide moiety and can be tolerated in any subsequent reactions of the resultant product. Alternatively, it may be desirable to maintain protection of the hydroxy group during reaction of the benzyl or benzal halide moiety and/or in reactions of the resultant product and thereafter conduct the deblocking reaction. The present invention provides flexibility in this respect in that a variety of protecting groups removable under a range of conditions can be employed herein.

Protecting groups capable of removal under acidic conditions, e.g., alkyl, tetrahydrofuranyl, tetrahydropyranyl, and phenacyl, can be removed in the presence of, for example, mineral acids such as hydrobromic acid or in the presence of boron tribromide. Protecting groups capable of removal under basic conditions, e.g., acyl, ethoxycarbonyl, and 2,2,2-trichloroethoxycarbonyl can be removed in the presence of, for example, aqueous alkali hydroxides such as aqueous sodium hydroxide and aqueous potassium hydroxide so as to generate hydroxy anion moieties which can be protonated by treatment with acid.

The following examples are given to further illustrate the present invention. It will be understood that the specific limitations set forth in the following examples are intended as being illustrative and not limitative.

EXAMPLE 1

Preparation of 4'-bromomethyl-2,5-dimethoxy-1,1'-biphenyl.

(a) To a suspension of 138 g. (0.69 mole) of 4'-methyl-2,5-dihydroxy-1,1'-biphenyl in 600 ml. of deaerated water at 70° C. were added simultaneously 270 g. of a deaerated 50% (w/w) aqueous solution of sodium hydroxide (3.38 moles NaOH) and 258 g. (2.05 moles) of dimethylsulfate over 30 minutes with stirring under a nitrogen atmosphere. The temperature during the addition was maintained at 80°-87° C. After stirring overnight at ambient temperature of about 25° C., 86 g. (0.68 mole) of dimethyl sulfate and 90 g. of 50% (w/w) aqueous sodium Hydroxide (1.13 moles NaOH) were added simultaneously and stirring continued an additional 24 hours. The reaction mixture was then chilled in ice, the tan colored crystals filtered, washed well with water and dried in a vacuum oven. After recrystallization in methanol, followed by drying in a vacuum oven, 120 g. of 4'-methyl-2,5-dimethoxy-1,1'-biphenyl were obtained having a melting range 65°-66° C.

(b) A mixture of 22.8 g. (0.1 mole) of 4'-methyl-2,5-dimethoxy-1,1'-biphenyl prepared in accordance with step (a) above, 18 g. (0.1 mole) N-bromosuccinimide, and 0.24 g. (0.001 mole) of dibenzoyl peroxide in 300 ml. carbon tetrachloride was heated at reflux for 18 hours. The reaction mixture was cooled and the precipitated succinimide removed by filtration. The solvent was removed on a rotary evaporator yielding 30.7 g. of a thick syrupy residue comprising a mixture of brominated products comprising, in major proportion, 4'-bromomethyl-2,5-dimethoxy-1,1'-biphenyl.

EXAMPLE 2

Preparation of 4'-bromomethyl-2,5-diacetoxy-1,1'-biphenyl:

(a) 100 Grams of 4'-methyl-2,5-dihydroxy-1,1'-biphenyl (0.5 mole) were suspended in 220 ml. of acetic anhydride and about 5 drops of sulfuric acid were added. The resultant solution was stirred at room temperature of about 25° C. for about 16 hours. Formation of a crystalline precipitate was observed. The reaction mixture was poured into ice-water and the resultant white precipitate was separated by filtration, washed with water, and dried in a vacuum oven at 60° C. for 3 days. A yield of 140 g. of 4'-methyl-2,5-diacetoxy-1,1'-biphenyl was obtained. The product had a melting range of 94°-96° C.

(b) A mixture of 28.4 g. (0.1 mole) of 4'-methyl-2,5-diacetoxy-1,1'-biphenyl prepared in section (a) of this Example, 18.7 g. (0.105 mole) of N-bromosuccinimide, and 0.25 g. (0.001 mole) of dibenzoyl peroxide in 250 ml. of carbon tetrachloride was heated at reflux for about 6 hours. The mixture was cooled and the precipitated succinimide was removed by filtration. The filtrate solvent was removed on a rotary evaporator yielding about 42 g. of a syrupy residue. The residue was mixed with 80 ml. of low boiling petroleum ether, the mixture heated to reflux with stirring, and the petroleum ether decanted. This extraction process was repeated twice more yielding 35.5 g. of a syrupy residue. This residue was then dissolved in 180 ml. of diethylether and the solution diluted with 120 ml. of n-hexanes. Cooling of the solution in dry-ice and scratching the sides of the container induced crystallization of the product. A first crop of 17.2 g. of 4'-bromomethyl-2,5-diacetoxy-1,1'-biphenyl was obtained. The mother liquor was concentrated and crystallization induced as above to yield an additional 6.5 g. of product. The procedure was repeated once again to yield a third crop of 8.3 g. Total yield was thus 32.0 g. Nuclear magnetic resonance analysis of the combined product in deuterochloroform was consistent with the structure of 4'-bromomethyl-2,5-diacetoxy-1,1'-biphenyl. The melting range of the product was 51°-53° C.

As mentioned previously, the compounds of this invention can be utilized to prepare useful redox polymers. The following EXAMPLE is included herein to illustrate such preparation:

EXAMPLE 3

(a) The 30.7 g. of syrupy residue prepared in Example 1 and comprising, in major proportion, 4'-bromethyl-2,5-dimethoxy-1,1'-biphenyl, was dissolved in 300 ml of tetrahydrofuran, 26.2 g. (0.1 mole) of triphenylphosphine added, and the mixture stirred at ambient temperature of about 25° C. for 16 hours. The mixture was then refluxed for one hour, cooled, and the resultant precipitate filtered, washed first with benzene and then tetrahydrofuran, and dried in a vacuum oven at 60° C. Yield of 38 g. of material. NMR spectrum in CDCl$_3$ showed three different methoxyl resonances as would be expected from a mixture of 4'-(triphenylphosphonium)-methyl-2,5,-dimethoxy-1,1'-biphenyl bromide and 4'-(triphenylphosphonium)methyl-4-bromo-2,5-dimethoxy-1,1'-biphenyl bromide.

(b) The 38 g. of material obtained in step (a) were suspended in 66 ml. of a 37% (w/w) aqueous formaldehyde solution and 25 ml. of a 50% (w/w) solution of sodium hydroxide were added dropwise with stirring over 30 minutes. After stirring for 2 hours, the reaction mixture was extracted with methylene chloride, the extract washed with water and saturated sodium chloride solution, and dried over anhydrous sodium sulfate. Removal of the solvent on a rotary evaporator left 10.3 g. of a residue which was extracted with n-hexane. The n-hexane was evaporated to yield 4.8 g. of a mixture comprising 4'-vinyl-2,5-dimethoxy-1,1'-biphenyl and 4'-vinyl-4-bromo-2,5-dimethoxy-1,1'-biphenyl. The mixture was chromatographed on 150 g. of Florisil adsorbent (commercially available from the Floridin Co., Pittsburgh, Pa.) using a 60:40 by volume mixture of hexane and toluene. 2.9 g. of 4'-vinyl-2,5-dimethoxy-1,1'-biphenyl were obtained as an oil. Elemental analysis calculated for $C_{16}H_{16}O_2$: C, 79.97; H, 6.71. Found: C, 79.53; H, 6.80.

(c) A solution of 2 g. of the 4'-vinyl-2,5-dimethoxy-1,1'-biphenyl prepared in section (b) of this Example and 0.07 g. azobisisobutyronitrile in benzene was deaerated with nitrogen and sealed in a glass tube under vacuum. The solution was heated at 63° C. for 48 hours. The contents of the tube were cooled and poured with stirring into 250 ml. of methanol. The precipitated linear polymer was filtered, washed with methanol, and dried in a vacuum oven. Yield of 1.7 g. of poly(4'-vinyl-2,5-dimethoxy-1,1'-biphenyl). Elemental analysis calculated for $C_{16}H_{16}O_2$: C, 79.97; H, 6.71. Found: C, 79.62; H, 6.27.

(d) To a solution of 1.2 g. of the poly(4'-vinyl-2,5-dimethoxy-1,1'-biphenyl) prepared in section (c) of this Example, in 10 ml. of methylene chloride, under nitrogen and cooled to −50° C., was added dropwise a solution of 1.2 ml. of boron tribromide in 4 ml. of methylene chloride. The addition was carried out over 20 minutes. The mixture was allowed to warm to ambient temperature and stirred overnight. It was then refluxed for one hour, cooled and poured into ice-water containing 6 g. of sodium acetate trihydrate. Methylene chloride was removed by bubbling nitrogen through the mixture and the linear homopolymer was isolated by decantation and washed with ether. Dissolution of the polymer in methanol followed by precipitation into water under nitrogen gave 0.8 g. of linear poly(4'-vinyl-2,5-dihydroxy-1,1'-biphenyl) as an off-white solid. NMR in d$_6$-DMSO was consistent with the structure. The polymer was soluble in aqueous alkali. Elemental analysis calculated for $C_{14}H_{12}O_2$: C, 79.22; H, 5.70. Found: C, 78.9; H, 5.5.

The poly(4'-vinyl-2,5-dihydroxy-1,1'-biphenyl) prepared in this Example was dissolved in aqueous sodium hydroxide. The solution was applied to a previously exposed silver halide emulsion layer coated on a paper support. After several minutes the silver halide emulsion blackened indicating development thereof by the dissolved polymer, i.e., reduction of the silver halide to silver metal.

Polymeric redox materials prepared utilizing the intermediates of this invention are capable of participating in oxidation-reduction reactions and, accordingly, may be employed in a variety of applications, e.g., as antioxidants or, in a photographic application, as immobile scavengers for oxidized silver halide developing agents.

EXAMPLE 4

Preparation of 4'-dibromomethyl-2,5-diacetoxy-1,1'-biphenyl:

A mixture of 13.0 g. (0.046 mole) of 4'-methyl-2,5-diacetoxy-1,1'-biphenyl, prepared as described in Example 2(a), 18. g. (0.1 mole) of N-bromosuccinimide, and 0.5 g. of dibenzoyl peroxide (0.0005 mole) in 150 ml. of carbon tetrachloride was heated at reflux for about 15 hours. The mixture was cooled and the precipitated succinimide was removed by filtration. The filtrate was washed with cold water and dried over anhydrous sodium sulfate. The filtrate solvent was removed on a rotary evaporator yielding a solid. The solid was recrystallized from a 2:1 by volume mixture of hexane:ether, yielding about 15.6 g. of 4'-dibromomethyl-2,5-diacetoxy-1,1'-biphenyl, m.p. 95°–97° C. The product gave a single spot on TLC (Whatman K5F Silica Gel; 20% n-hexane, 80% chloroform eluent) and proton nuclear magnetic resonance and infrared spectral data confirmed the structure of the product.

The following Examples 5 and 6 provide illustrative preparations of 4'-formyl-2,5-dihydroxy-1,1'-biphenyl employing, respectively, 4'-bromomethyl-2,5-diacetoxy-1,1'-biphenyl and 4'-dibromomethyl-2,5-diacetoxy-1,1'-biphenyl as starting materials.

EXAMPLE 5

A solution of 3.63 g. (0.01 mole) of 4'-bromomethyl-2,5-diacetoxy-1,1'-biphenyl and 1.04 g. (0.01 mole) of hexamethylenetetramine in 40 ml. of acetonitrile was heated at reflux under nitrogen for about 6 hours. The solution was cooled, the solvent removed on a rotary evaporator, and the resultant residue dissolved in 30 ml. of methanol. The methanol solution was diluted with 100 ml. of water and 10 ml. of concentrated hydrochloric acid and heated at reflux under nitrogen for about 1 hour. Most of the methanol was then removed on a rotary evaporator and the concentrated mixture was diluted with water and cooled to give 1.2 g. of 4'-formyl-2,5-dihydroxy-1,1'-biphenyl as an off-white solid, m.p., 202°–204° C. Thin layer chromatography indicated one component and proton nuclear magnetic resonance and infrared spectral data confirmed the structure of the product.

EXAMPLE 6

A mixture of about 4.4 g. (0.01 mole) of 4'-dibromomethyl-2,5-diacetoxy-1,1'-biphenyl and about 4.4 g. (0.03 mole) of sodium acetate trihydrate in a mixture of 50 ml. methanol and 25 ml. of water was heated at reflux under nitrogen for about 4 hours. 5 ml. of concentrated hydrochloric acid were added and refluxing continued for an additional 1½ hours. Most of the methanol was removed by evaporation on a steam bath under nitrogen resulting in precipitation of a light cream colored solid. The mixture was diluted with 50 ml. of water, cooled in an ice bath, and the resultant solid filtered, washed with water, and dried in a vacuum oven. Yield of about 2.0 g. of 4'-formyl-2,5-dihydroxy-1,1'-biphenyl, m.p. 203°–205° C. Thin layer chromatography indicated one component. Proton nuclear magnetic resonance and infrared spectra confirmed the structure and were essentially identical to the spectra obtained from the product of Example 5. The product gave a positive test with 2,4-dinitrophenylhydrazine spray reagent.

Since certain changes may be made in the above products and processes without departing from the scope of the invention herein involved, it is intended that all matter contained in the above description shall be interpreted as illustrative and not in a limiting sense.

What is claimed is:

1. A compound of the formula

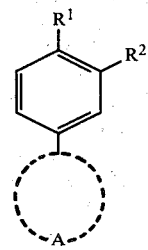

wherein one of $R^1$ and $R^2$ is hydrogen and the other is $CH_{3-m}X_m$ wherein X is chloro or bromo and m is an integer one or two, and the cyclic moiety A is a -2,5-; -2,3-; or -3,4-di-OR-1-phenyl moiety of the formula

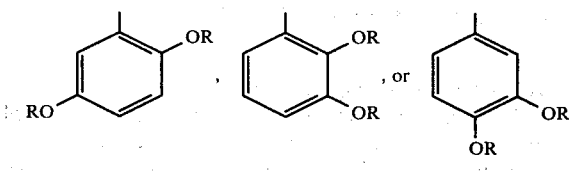

wherein R is a hydroxy-protecting group capable of removal so as to regenerate the hydroxy group.

2. A compound of claim 1 wherein said R is selected from the group consisting of lower alkyl having 1 to 6 carbon atoms, methoxymethyl, methylthiomethyl, phenacyl, p-bromophenacyl, 2-tetrahydrofuranyl, 2-tetrahydropyranyl, ethoxycarbonyl, 2,2,2-trichloroethoxycarbonyl, and acyl.

3. A compound of claim 2 wherein said R is lower alkyl having 1 to 6 carbon atoms.

4. A compound of claim 3 wherein said R is methyl.

5. A compound of claim 1 wherein said R is an electron-withdrawing group.

6. A compound of claim 5 wherein said R is selected from the group consisting of acyl, ethoxycarbonyl, and 2,2,2-trichloroethoxycarbonyl.

7. A compound of claim 6 wherein said R is acyl.

8. A compound of claim 7 wherein said R is acetyl.

9. A compound of claim 1 wherein X is bromo.

10. A compound of claim 1 wherein m is one.

11. A compound of claim 1 wherein m is two.

12. A compound of the formula

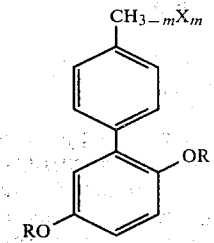

wherein X is chloro or bromo, R is a hydrogen-protecting group capable of removal so as to regenerate the hydroxy group, and m is an integer one or two.

13. A compound of claim 12 wherein X is bromo.

14. A compound of the formula

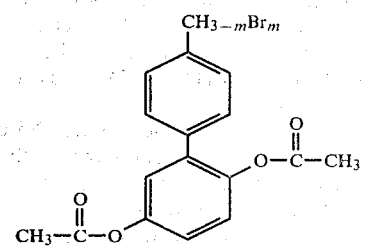

wherein m is an integer one or two.

15. A compound of the formula

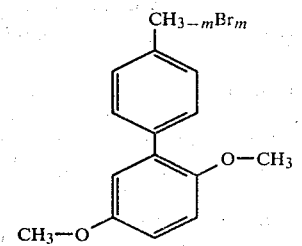

wherein m is an integer one or two.

16. A compound of claim 15 wherein m is one.

* * * * *